United States Patent [19]

Gerster et al.

[11] Patent Number: 4,929,624

[45] Date of Patent: May 29, 1990

[54] OLEFINIC 1H-IMIDAZO(4,5-C)QUINOLIN-4-AMINES

[75] Inventors: John F. Gerster; Roy T. Knafla, both of Woodbury, Minn.

[73] Assignee: Minnesota Mining and Manufacturing Company, St. Paul, Minn.

[21] Appl. No.: 327,693

[22] Filed: Mar. 23, 1989

[51] Int. Cl.$^5$ .......................................... C07D 471/02
[52] U.S. Cl. ..................................... 514/293; 546/82; 546/159
[58] Field of Search ................... 546/82, 159; 514/293

[56] References Cited

U.S. PATENT DOCUMENTS

| | | | |
|---|---|---|---|
| 4,552,874 | 11/1985 | Mardin et al. | 514/222 |
| 4,563,525 | 1/1986 | Campbell et al. | 546/82 |
| 4,689,338 | 8/1987 | Gerster . | |
| 4,698,346 | 10/1987 | Musser et al. | 514/293 |
| 4,698,348 | 10/1987 | Gerster . | |

OTHER PUBLICATIONS

J. Org. Chem 15, 1278–1284 (1950), Backman et al.
J. Med. Chem. 11, pp. 87–92 (1968), Jain et al.
Chem. Abs. 85, 94362 (1976), Baranov et al.
J. Heterocyclic Chem. 18, 1537–1540 (1981), Berenyi et al.

*Primary Examiner*—Mary C. Lee
*Assistant Examiner*—Catherine S. Scalzo
*Attorney, Agent, or Firm*—Donald M. Sell; Walter N. Kirn; Robert W. Sprague

[57] ABSTRACT

Novel 1-substituted 1H-imidazo-[4,5-c]quinolin-4-amines are disclosed. These compounds function as antiviral agents, and they are potential synthetic intermediates in the preparation of known antiviral agents and labeled known antiviral agents. This invention also provides intermediates for preparing such compounds, pharmaceutical compositions containing such compounds, and pharmacological methods of using such compounds.

7 Claims, No Drawings

OLEFINIC 1H-IMIDAZO(4,5-C)QUINOLIN-4-AMINES

BACKGROUND OF THE INVENTION

1. Field of the Invention

This invention pertains to 1H-imidazo[4,5-c]quinoline compounds. More particularly, this invention pertains to antiviral 1H-imidazo[4,5-c]quinolin-4-amine compounds, intermediates for the preparation of such compounds, pharmaceutical compositions containing such compounds, and pharmacological methods of using such compounds.

2. Description of the Related Art

The first reliable report of the 1H-imidazo[4,5-c]quinoline ring system, Backman et al., J. Org. Chem. 15, 1278–1284 (1950), describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c]quinolines have been reported. For example, Jain et al., J. Med. Chem. 11, pp. 87–92 (1968), has synthesized the compound 1-[2-(4-piperidyl)ethyl]-1H-imidazo[4,5-c]quinoline as a possible anticonvulsant and cardiovascular agent. Also, Baranov et al., Chem. Abs. 85, 94362 (1976), has reported several 2-oxoimidazo[4,5-c]quinolines, and Berenyi et al., J. Heterocyclic Chem. 18, 1537–1540 (1981), has reported certain 2-oxoimidazo[4,5-c]quinolines.

Certain 1H-imidazo[4,5-c]quinolin-4-amines are described in U.S. Pat. No. 4,689,338. These compounds are substituted on the 1-position by alkyl, hydroxyalkyl, acyloxyalkyl, benzyl, phenylethyl or substituted phenylethyl, and are useful as antiviral agents. Furthermore, these compounds are known to induce interferon biosynthesis.

DETAILED DESCRIPTION OF THE INVENTION

This invention provides novel compounds of Formula I:

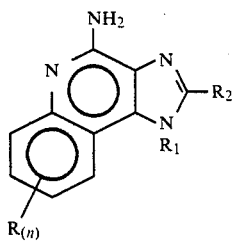

wherein $R_1$ is selected from the group consisting of straight chain or branched chain alkenyl containing 2 to about 10 carbon atoms and substituted straight chain or branched chain alkenyl containing 2 to about 10 carbon atoms, wherein the substituent is selected from the group consisting of straight chain or branched chain alkyl containing 1 to about 4 carbon atoms, cycloalkyl containing 3 to about 6 carbon atoms and cycloalkyl containing 3 to about 6 carbon atoms substituted by straight chain or branched chain alkyl containing 1 to about 4 carbon atoms; and $R_2$ is selected from the group consisting of hydrogen, straight chain or branched chain alkyl containing one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl containing one to about four carbon atoms, straight chain or branched chain alkoxy containing one to about four carbon atoms, and halogen, with the proviso that when the benzene ring is substituted by two such moieties, then the moieties together contain no more than 6 carbon atoms; and each R is independently selected from the group consisting of straight chain or branched chain alkoxy containing one to about four carbon atoms, halogen, and straight chain or branched chain alkyl containing one to about four carbon atoms, and n is an integer from zero to 2, with the proviso that if n is 2, then said R groups together contain no more than 6 carbon atoms; or a pharmaceutically acceptable acid addition salt thereof. Compounds of Formula I are useful as antiviral agents.

For the purposes of the instant specification and claims, the term "lower" when used in conjunction with "alkyl" or "alkoxy" designates straight chain or branched chain substituents containing 1 to about 4 carbon atoms.

$R_1$ preferably contains two to about ten carbon atoms. More preferably $R_1$ contains two to about eight carbon atoms. Most preferably, $R_1$ is ethenyl, 1-propenyl, 2-propenyl, or ethenyl or 2-propenyl substituted by lower alkyl.

$R_2$ is preferably benzyl, phenylethyl, lower alkyl, or hydrogen, most preferably lower alkyl or hydrogen.

Other substituents that contain an alkyl radical (e.g., R when R is alkoxy or alkyl, or lower alkyl or lower alkoxy substituents on $R_1$) preferably contain two carbon atoms or, more preferably, one carbon atom in each alkyl radical.

The halogen substituents are selected from fluorine, chlorine and bromine. Preferred halogen substituents are fluorine and chlorine.

It is preferred that n of Formula I be zero or one. It is most preferred that n of Formula I be zero.

Presently preferred compounds are: 1-(2-methyl-2-propenyl)-1H-imidazo[4,5-c]quinolin-4-amine; and 1-(2-methyl-1-propenyl)-1H-imidazo[4,5-c]quinolin-4-amine.

A compound of the invention of Formula I can be prepared as described in the Reaction Scheme illustrated below, wherein R, $R_1$, $R_2$ and n are as defined above and $R_{OH}$ is a latent $R_1$ substituent, e.g., hydroxyalkyl or like substituent comprising a leaving group susceptible to removal by an elimination, dehydration, or like reaction well known to those skilled in the art, to afford a substituent $R_1$ as described above.

Reaction Scheme

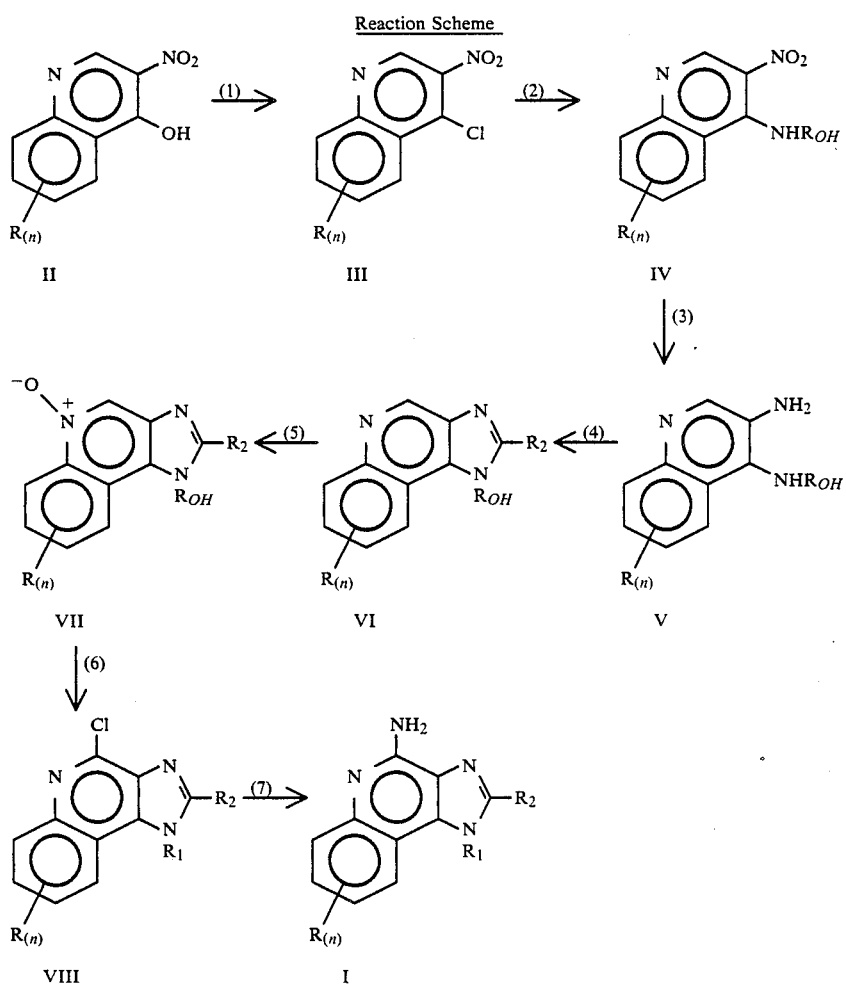

Such $R_{OH}$ substituents include 2-hydroxyethyl, 2 hydroxy-2-methylpropyl, 2-hydroxy-1-methylethyl, 2,2-dimethyl-2-hydroxypropyl, and the like. Tertiary hydroxy groups are preferred, because they are more susceptible to removal.

Many quinolines of Formula III are known compounds (see, for example, U.S. Pat. No. 3,700,674 and references cited therein). Those that are not known can be prepared by known methods, for example, from 4-hydroxy-3-nitroquinolines as illustrated in step (1) of the Reaction Scheme. Step (1) can be conducted by reacting the 4-hydroxy-3-nitroquinoline of Formula II with phosphorus oxychloride. The reaction is preferably conducted in N,N-dimethylformamide and is preferably accompanied by heating. Preferably, a large molar excess of phosphorus oxychloride is avoided. Use of about 1–2 moles of phosphorus oxychloride per mole of the 4-hydroxy-3-nitroquinoline of Formula II has been found to be particularly preferable.

In step (2) a 3-nitro-4-chloroquinoline of Formula III is reacted by heating with an aminoalcohol of the formula $R_{OH}NH_2$, wherein $R_{OH}$ is as defined above, in a suitable solvent such as water, dichloromethane, or tetrahydrofuran, to provide a quinoline of Formula IV. Some of the compounds of Formula IV are novel.

Steps (1) and (2) can be combined such that the 3-nitro-4-chloroquinoline need not be isolated prior to reaction with the compound of the formula $R_{OH}NH_2$. Such a reaction is exemplified in Example 134 and Example 188 (Step A) of U.S. Pat. No. 4,689,338, the disclosure of which is incorporated herein by reference.

A compound of Formula IV is reduced in step (3) preferably using a catalyst such as platinum on charcoal, to provide a compound of Formula V. The reduction can be carried out conveniently on a Paar apparatus in an inert solvent such as toluene or a lower alkanol. Some compounds of Formula V are novel.

In step (4) an intermediate compound of Formula V is reacted with (i) a 1,1-dialkoxyalkyl alkanoate such as diethoxymethyl acetate, or (ii) a carboxylic acid of the formula $R_2CO_2H$, which will introduce the desired $R_2$ group, or (iii) a trialkyl ortho ester of the formula $R_2C(Oalkyl)_3$, wherein "alkyl" is a straight chain or branched chain alkyl group containing 1 to about 4 carbon atoms, or (iv) a combination of such a carboxylic acid with such a trialkyl ortho ester to provide a compound of Formula VI. The reaction can be carried out by heating, e.g., at about 130° C., in the presence of an acid, preferably a carboxylic acid of the formula $R_2CO_2H$. Some of the compounds of Formula VI are novel.

Step (5) provides an intermediate of Formula VII, through oxidation of a compound of Formula VI with a conventional oxidizing agent that is capable of forming N-oxides but does not oxidize a hydroxyl group on $R_{OH}$ if one is present. If, however, $R_{OH}$ is not capable of oxidation, a wider range of conventional oxidizing agents is useful. Preferred oxidizing agents include peroxyacids and hydrogen peroxide. The oxidation reaction is preferably conducted in glacial acetic acid. Heating is generally employed to accelerate the rate of reaction.

It is sometimes useful to protect a hydroxy group, with, for example, an alkanoyloxy group such as acetoxy or with benzoyloxy, for step(s) (5) and/or (6) and/or (7), and then to remove the protecting group and eliminate to form the compound of Formula I. Such protecting groups and reactions for their placement and removal are well known to those skilled in the art. See, for example, U.S. Pat. No. 4,689,338, Examples 115 to 123.

Step (6) as illustrated is a step particularly amenable to compounds of Formula VII wherein $R_{OH}$ is a hydroxyalkyl group in which the hydroxyl group is capable of elimination to form an $R_1$ substituent. In step (6) an N-oxide of Formula VII is heated in the presence of a suitable chlorinating agent such as phosphorus oxychloride to provide an intermediate of Formula VIII. Two reactions occur: (1) the N-oxide is removed with concommitant chlorination of the 4-position, and (2) the hydroxyl group is eliminated to form the olefinic double bond of $R_1$. In practice, this elimination has occurred without external heating and in various solvents, particularly in larger scale reactions. This is thought to be a result of localized overheating. The best synthetic results are obtained by refluxing a compound of Formula VII in neat phosphorus oxychloride. Alternatives to step (6) that are useful for compounds of Formula VII wherein $R_{OH}$ comprises a leaving group other than hydroxyl include, for example, first eliminating the leaving group to form the olefinic double bond of $R_1$, and subjecting the resulting compound to the chlorination conditions recited above in connection with step (6) to form a compound of Formula VIII.

In step (7) the 4-chloro group is replaced by a 4-amino group to provide a compound of Formula I. The reaction is carried out in the presence of ammonium hydroxide or, preferably, ammonia. Preferably the intermediate of Formula VIII is heated at 125° to 175° C. under pressure for 6–24 hours. Preferably the reaction is conducted in a sealed reactor in the presence of either ammonium hydroxide or a solution of ammonia in an alkanol, (e.g., preferably about 15% ammonia in methanol).

The reaction sequence illustrated in the Reaction Scheme is not intended to represent the only route by which a compound of Formula I can be prepared, and alternative routes will be contemplated by those skilled in the art.

The compounds of the invention can be readily reduced by methods well known to those skilled in the art to provide known antiviral agents substituted at the 1-position with alkyl, disclosed in U.S. Pat. No. 4,689,338. Also, should it be desired for the purposes of metabolic studies to prepare such a known antiviral agent with a label, e.g., a radiolabel such as tritium, on the alkyl group, the olefinic double bond of $R_1$ provides ready functionality for use in preparing such a labeled compound.

A compound of Formula I can be used as an antiviral agent itself or it can be used in the form of a pharmaceutically acceptable acid-addition salt such as a hydrochloride, dihydrogen sulfate, trihydrogen phosphate, hydrogen nitrate, methane sulfonate or a salt of another pharmaceutically acceptable acid. A pharmaceutically acceptable acid-addition salt of a compound of Formula I can be prepared, generally by reaction of the compound with an equimolar amount of a relatively strong acid, preferably an inorganic acid such as hydrochloric, sulfuric, or phosphoric acid, or an organic acid such as methanesulfonic acid, in a polar solvent. Isolation of the salt is facilitated by the addition of a solvent, such as diethyl ether, in which the salt is insoluble.

A compound of the invention can be formulated for the various routes of administration in a pharmaceutically acceptable vehicle, such as water or polyethylene glycol, along with suitable adjuvants, excipients, and the like. Particular formulations will be easily selected by those skilled in the art. Suitable formulations for topical application include creams, ointments and like formulations known to those skilled in the art, and generally contain less than 10% by weight of a compound of Formula I, preferably about 0.1% to 5% by weight of a compound of Formula I.

The compounds of the invention exhibit antiviral activity in mammals and can therefore be used to control viral infections. A preferred use of a compound of the invention is as an agent to control infections in mammals caused by Type I or Type II Herpes simplex virus. Generally, treatment is effective when a compound of Formula I or a formulation thereof is administered topically (e.g., intravaginally or on the skin), to a herpes infection. Compounds of Formula I can also be used to treat a herpes infection by oral or intraperitoneal administration.

The anti-Herpes activity of the compounds of Formula I relative to primary lesions caused by Type I or Type II Herpes simplex virus was demonstrated using the method described generally by Kern, et al., Antimicrob. Agents Chemother. 14, 817–823 (1978).

This method uses female guinea pigs of 200 to 300 grams in weight, preferably 200 to 260 grams in weight. Hartley guinea pigs are the preferred strain. The guinea pigs are anesthetized with pentobarbital or methoxyflurane, and then infected intravaginally, using a cotton swab, with about $10^5$ plaque forming units of Herpes simplex virus, either type I or type II. A compound of Formula I is formulated preferably in saline or water using a surfactant such as "Tween 80" (a polyoxyethylene sorbitan monooleate, commercially available from Emulsion Engineering Inc., Elk Grove Village, Ill.). Alternatively, a compound of Formula I can be formulated in "PEG 400" (a polyethyleneglycol of average molecular weight of about 400, commercially available from Union Carbide Corporation), or in polyethyleneglycol cream. Application of the formulation is initiated at the predetermined interval after infection such as one hour after infection. The formulation is applied intravaginally, for example, twice daily for a predetermined number of days, typically five or seven days. Virus replication can be monitored by determining the amount of virus recovered with vaginal swabs taken, for example, on days 1, 2, 3, 5 or 7 after infection. Virus is eluted from the swab in 1 ml of cell growth medium (Medium 199, Gibco Laboratories, Grand Island, N.Y.) and virus titer is determined using cell monolayers. External lesions are scored daily for 10 days using the following scale: zero, no lesions; 1, redness or swelling; 2, a few small vesicles; 3, several large vesicles; 4, large ulcers and necrosis; 5, paralysis. The degree of inhibition of lesion development is determined by comparing lesion development in infected and untreated control animals to lesion development in infected and drug-treated animals. Comparison studies with known drugs such as phosphonacetic acid and acyclovir can also be conducted. The compounds of the invention reduce the number of lesions and the severity thereof.

The compounds of Formula I induce biosynthesis of interferon, and they function as immunomodulators. It is believed that the antiviral activity exhibited by compounds of Formula I is attributable to this induction of interferon biosynthesis. That biosynthesis of interferon or an interferon-like substance is induced suggests that at least certain compounds of the invention might be useful in treating other diseases such as rheumatoid arthritis, warts, eczema, Hepatitis B, psoriasis, multiple sclerosis, essential thrombocythaemia, cancer such as basal cell carcinoma, and other neoplastic diseases.

The following examples are provided to illustrate the invention and are not intended to be limiting thereof.

EXAMPLE 1

Preparation of a Compound of Formula IV.

To a stirred solution of 150 ml of dichloromethane, 10 ml of triethylamine and 6.7 g (0.075 mole) of 1-amino-2-methyl-2-propanol was added 10.4 g (0.05 mole) of 4-chloro-3-nitroquinoline. The solution was heated on a steam bath for about one hour then evaporated to remove the solvent. The residue was dissolved in dilute hydrochloric acid and filtered. The filtrate was made basic with concentrated ammonium hydroxide to reprecipitate the product. The product was separated by filtration and recrystallized twice from ethanol to provide the novel yellow solid 2-methyl-1-[(3-nitro-4-quinolinyl)amino]-2-propanol, m.p. 244°–246° C. (dec.). Analysis: Calculated for $C_{13}H_{15}N_3O_3$: %C, 59.8; %H, 5.8; %N, 16.0; Found: %C, 59.8; %H, 5.9; %N 16.1.

EXAMPLE 2

Using the method of Example 1, 4-chloro-3-nitroquinoline was reacted with 2-amino-2-methyl-1-propanol to afford 2-[(3-nitro-4-quinolinyl)amino]-1-propanol, m.p. 207°–211° C. Analysis: Calculated for $C_{12}H_{13}N_3O_3$: %C, 58.3; %H, 5.3; %N, 17; Found: %C, 58.6; %H, 5.3; %N, 17.2.

EXAMPLE 3

Preparation of a Compound of Formula V.

To a solution of 7.0 g (0.027 mole) of 2-methyl-1-[(3-nitro-4-quinolinyl)amino]-2-propanol (from Example 1) in 150 ml of ethanol and 200 ml of toluene was added about 1 g of 5% platinum on charcoal, and the mixture was hydrogenated on a Paar apparatus until no further reaction occurred. Filtration followed by evaporation in vacuo provided a residue which gradually solidified to yellow solid 2-methyl-1-[(3-amino-4-quinolinyl)amino]-2-propanol.

EXAMPLE 4

Preparation of a Compound of Formula V.

A mixture of 27.9 g (0.113 mole) of 2-[(3-nitro-4-quinolinyl)amino]-1-propanol in 1.2 l of ethyl acetate, 28 g of magnesium sulfate and 2.0 g of 5% platinum on charcoal was hydrogenated on a Paar apparatus until hydrogen uptake was completed. The catalyst and solid residue were removed by filtration and the filtrate was concentrated by evaporation to provide 2-[(3-amino-4-quinolinyl)amino]-1-propanol as a yellow oil.

EXAMPLE 5

Preparation of a Compound of Formula VI.

2-Methyl-1-[(3-amino-4-quinolinyl)amino]-2-propanol, (0.027 mole), a crude reaction product obtained by the method of Example 3 was mixed with 5 drops of 98% formic acid and 50 ml of triethyl orthoformate, and the resulting mixture was heated at 135°–140° C. for one hour. Evaporation provided a residue which was dissolved in dilute hydrochloric acid. The solution was basified with concentrated sodium hydroxide. The solid was separated by filtration and washed with water to provide alpha, alpha-dimethyl-1H-imidazo[4,5-c]quinoline-1-ethanol. When a sample of this product was recrystallized from ethyl acetate it had a melting point of 169°–170° C. Analysis: Calculated for $C_{14}H_{15}N_3O.H_2O$: %C, 64.8; %H, 6.6; %N, 16.2; Found: %C, 65.1; %H, 6.6; %N, 16.4.

EXAMPLE 6

Alternative Preparation of a Compound of Formula VI.

2-[(3-Amino-4-quinolinyl)amino]-1-propanol (0.113 mole) as a crude reaction product obtained by the method of Example 4, was mixed with a 20 percent molar excess of diethoxymethyl acetate (22.3 g, 0.136 mole) and heated for 0.75 hour. To the mixture was added 150 ml of water. The resulting mixture was made basic with concentrated ammonium hydroxide, and extracted first with ethyl acetate, then with chloroform. The extracts were combined, dried over magnesium sulfate, and evaporated, slurried in 1:1 chloroform/diethyl ether and separated by filtration to provide the solid product, beta-methyl-1H-imidazo[4,5-c]quinoline-1-ethanol, m.p. 170°–174° C. after recrystallization from ethanol with treatment with decolorizing carbon. Analysis: Calculated for $C_{13}H_{13}N_3O$: %C, 68.7; %H, 5.8; N, 18.5; Found: %C, 68.5; %H, 5.8; %N, 18.5.

EXAMPLE 7

Preparation of a Compound of Formula VII.

To a solution of 24.1 g (0.10 mole) of alpha, alpha-dimethyl-1H-imidazo[4,5-c]quinoline-1-ethanol (from Example 5) in 250 ml of acetic acid was added 22.6 g (0.20 mole) of 30% hydrogen peroxide. The mixture was heated at 65°–70° C. for 6 hours and was then evaporated. The residue was dissolved in water and then basified with saturated sodium bicarbonate solution, and the product precipitated. The product was separated by filtration, washed with water and dried. The solid was slurried with acetone, filtered, washed with acetone and dried to provide alpha, alpha-dimethyl-1H-imidazo[4,5-c]quinoline-1-ethanol-5-oxide.

EXAMPLE 8

Acetylation and N-Oxidation of a Compound of Formula VI.

A mixture of 13.1 g (0.058 mole) of beta-methyl-1H-imidazo[4,5-c]quinoline-1-ethanol and 35 ml of acetic anhydride was heated at about 100° C. for two hours. To this solution was added 350 ml of methanol and the solution was stirred for about 0.5 hour. The solution was evaporated in vacuo and the residue was added to a saturated sodium bicarbonate solution. The mixture was extracted with chloroform, the extracts were dried over magnesium sulfate and concentrated to a volume of about 150 ml. To this solution was added 15 g (0.07 mole) of meta-chloroperbenzoic acid. The mixture was stirred for one hour, then washed with chloroform, saturated sodium bicarbonate solution and water. The organic layer was then dried over magnesium sulfate and concentrated by evaporation in vacuo to provide 1-(2-acetoxy-1-methylethyl)-1H-imidazo[4,5-c]-quinolin-5-oxide.

EXAMPLE 9

Preparation of a Compound of Formula I

A mixture of about 0.1 g of 4-chloro-alpha, alpha-dimethyl-1H-imidazo[4,5-c]quinoline-1-ethanol and about 5 ml of phosphorus oxychloride was heated at its reflux temperature for 30 minutes. The mixture was poured over ice, then extracted with ethyl acetate. The extracts were analyzed by thin layer chromatography and found to contain a mixture of two isomers: 4-chloro-1-(2-methyl-1-propenyl)-1H-imidazo[4,5-c]quinoline and 4-chloro-1-(2-methyl-2-propenyl)-1H-imidazo[4,5-c]quinoline.

The mixture of isomers was chromatographed and separated on silica gel (grade 60), eluting with 1:1:1 ethyl acetate-dichloromethane-hexane. The slower moving fraction was determined to be 4-chloro-1-(2-methyl-2-propenyl)-1H-imidazo[4,5-c]quinoline by proton magnetic resonance spectral analysis.

The product 4-chloro-1-(2-methyl-2-propenyl)-1H-imidazo[4,5-c]quinoline from above was reacted with 18% methanolic ammonia as described in Example 10 below to yield a solid. The solid was extracted with hot ethanol, leaving an insoluble residue. The extracts were concentrated to about 20% of their original volume to provide white solid product, 1-(2-methyl-2-propenyl)-1H-imidazo[4,5-c]quinolin-4-amine, m.p. 290°–294° C. Analysis: Calculated for $C_{14}H_{14}N_4$: %C, 70.6; %H, 5.9; %N, 23.5; Found: %C, 70.6; %H, 6.0; %N, 23.6.

Similarly, the isomer 4-chloro-1-(2-methyl-1-propenyl)-1H-imidazo[4,5-c]quinoline was reacted with 19% ammonia in methanol to provide 1-(2-methyl-1-propenyl)-1H-imidazo[4,5-c]quinolin-4-amine, m.p. 284°–289° C. after recrystallization from ethanol. Analysis: Calculated for $C_{14}H_{14}N_4$: %C, 70.6; %H, 5.9; %N, 23.5; Found: %C, 70.6; %H, 5.9; %N, 23.4.

EXAMPLE 10

Preparation of a Compound of Formula I

A mixture of 5.0 g (0.019 mole) of a mixture of 4-chloro-1-(2-methyl-2-propenyl)-1H-imidazo[4,5-c]quinoline and 4-chloro-1-(2-methyl-1-propenyl)-1H-imidazo[4,5-c]quinoline and 50 ml of 15% ammonia in methanol was heated in a sealed reactor at 150° C. for 6 hours. The mixture was cooled to about 20° C., then with an ice bath. A solid was separated from the mixture by filtration, washed with methanol and dried. The solid was recrystallized from N,N-dimethylformamide, boiled in water and filtered hot, then recrystallized again from N,N-dimethylformamide. Proton magnetic resonance spectral analysis of the product indicated both isomers 1-(2-methyl-2-propenyl)-1H-imidazo[4,5-c]quinolin-4-amine and 1-(2-methyl-1-propenyl)-1H-imidazo[4,5-c]quinolin-4-amine were present. The presence of these two isomers was supported by a satisfactory elemental analysis. Calculated for $C_{14}H_{14}N_4$: %C, 70.6; %H, 5.9; %N, 23.5; Found: %C, 70.3; %H, 6.0; %N, 23.3.

EXAMPLE 11

A compound of Formula I could be combined with a catalyst such as platinum on charcoal in a suitable solvent such as ethanol and reduced with hydrogen in a Paar apparatus to provide a product according to Formula I wherein $R_1$ is alkyl.

EXAMPLE 12

Alternative Preparation of a Compound of Formula I

STEP A

To a stirred mixture of 10.2 g (0.036 mole) of 1-(2-acetoxy-1-methylethyl)-1H-imidazo[4,5-c]quinolin-5-oxide (prepared according to the method of Example 8) in 100 ml of dichloromethane was added in portions, 4.2 ml, 6.9 g (0.45 mole) of phosphorus oxychloride. After 4 hours the mixture was evaporated in vacuo. The residue was added to a saturated sodium bicarbonate solution, and that solution was extracted with chloroform. The chloroform layer was washed with both saturated sodium bicarbonate solution and water, dried over magnesium sulfate and evaporated in vacuo to yield light brown solid 1-(2-acetoxy-1-methylethyl)-4-chloro-1H-imidazo[4,5-c]quinoline.

STEP B

A portion of the solid from Step A (5.0 g) was added to 100 ml of 13% ammonia in methanol and 10 ml of ammonium hydroxide. The mixture was stirred for 60 hours and evaporated in vacuo. The residue was washed with saturated sodium bicarbonate solution and the solid residue was collected. The solid was washed with water and dried, then recrystallized from ethanol. The resulting solid was eluted through a silica gel column with ethyl acetate to provide deacetylated product, m.p. 173°–175° C. Analysis: Calculated for $C_{13}H_{12}N_3OCl$: %C, 59.7; %H, 4.6; %N, 16.1; Found: %C, 59.6; %H, 4.7; %N, 15.8.

STEP C

A sample of 5.0 g of the deacetylated product from Step B was combined with 75 ml of a solution of 13% ammonia in methanol in a sealed reactor and heated at 150° C. for six hours. The mixture was cooled to about 20° C., then evaporated. The solid residue was washed by slurrying in a solution of saturated sodium bicarbonate, separated by filtration, and dried. The solid was then recrystallized from 200 ml of ethanol to yield 2.4 g of 4-amino-alpha-methyl-1H-imidazo[4,5-c]quinoline-1-ethanol, m.p. 216°–221° C. Analysis: Calculated for $C_{13}H_{14}N_4O$: %C, 64.4; H, 5.8%; %O, 23.1%; Found: %C, 64.5; %H, 6.0; %O, 23.2.

The product from Step C could be converted to a compound of Formula I.

The claimed invention is:

1. A compound of the formula:

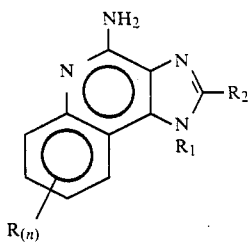

wherein $R_1$ is selected from the group consisting of straight chain or branched chain alkenyl containing 2 to about 10 carbon atoms and substituted straight chain or branched chain alkenyl containing 2 to about 10 carbon atoms, wherein the substituent is selected from the group consisting of straight chain or branched chain alkyl containing 1 to about 4 carbon atoms; cycloalkyl containing 3 to about 6 carbon atoms; and cycloalkyl containing 3 to about 6 carbon atoms substituted by straight chain or branched chain alkyl containing 1 to about 4 carbon atoms; and $R_2$ is selected from the group consisting of hydrogen, straight chain or branched chain alkyl containing one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl containing one to about four carbon atoms, straight chain or branched chain alkoxy containing one to about four carbon atoms, and halogen, with the proviso that when the benzene ring is substituted by two such moieties, then the moieties together contain no more than 6 carbon atoms; and each R is independently selected from the group consisting of straight chain or branched chain alkoxy containing one to about four carbon atoms, halogen, and straight chain or branched chain alkyl containing one to about four carbon atoms, and n is an integer from zero to 2, with the proviso that if n is 2, then said R groups together contain no more than 6 carbon atoms; or a pharmaceutically acceptable acid addition salt thereof.

2. A compound according to claim 1, selected from the group consisting of 1-(2-methyl-2-propenyl)-1H-imidazo[4,5-c]quinolin-4-amine, 1-(2-methyl-1-propenyl)-1H-imidazo[4,5-c]quinolin-4-amine, and a pharmaceutically acceptable acid addition salt of either.

3. A compound of the formula:

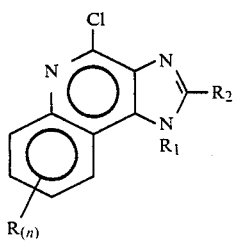

wherein $R_1$ is selected from the group consisting of straight chain or branched chain alkenyl containing 2 to about 10 carbon atoms and substituted straight chain or branched chain alkenyl containing 2 to about 10 carbon atoms, wherein the substituent is selected from the group consisting of straight chain or branched chain alkyl containing 1 to about 4 carbon atoms, cycloalkyl containing 3 to about 6 carbon atoms, and cycloalkyl containing 3 to about 6 carbon atoms substituted with straight chain or branched chain alkyl containing 1 to about 4 carbon atoms; and $R_2$ is selected from the group consisting of hydrogen, straight chain or branched chain alkyl containing one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl containing one to about four carbon atoms, straight chain or branched chain alkoxy containing one to about four carbon atoms, and halogen, with the proviso that when the benzene ring is substituted by two such moieties, then the moieties together contain no more than 6 carbon atoms; and each R is independently selected from the group consisting of straight chain or branched chain alkoxy containing one to about four carbon atoms, halogen, and straight chain or branched chain alkyl containing one to about four carbon atoms, and n is an integer from zero to 2, with the proviso that if n is 2, then said R groups together contain no more than 6 carbon atoms.

4. A antiviral pharmaceutical composition comprising a compound according to claim 1 and a pharmaceutically acceptable vehicle, the compound being present in an amount effective to inhibit and/or prevent the progress of a viral infection.

5. A method of treating a mammal infected with a virus, comprising administering to the mammal a compound according to claim 1 in an amount effective to inhibit and/or prevent the infection.

6. A method according to claim 5, wherein the virus is selected from the group consisting of Type I Herpes simplex and Type II Herpes simplex.

7. A method of inducing interferon biosynthesis in a mammal, which method comprises administering to the mammal a compound according to claim 1 in an amount sufficient to induce interferon biosynthesis.

* * * * *